(12) United States Patent
Mahoney et al.

(10) Patent No.: US 8,075,675 B2
(45) Date of Patent: Dec. 13, 2011

(54) APPARATUS AND METHOD FOR EXTRACTING GAS FROM LIQUID

(75) Inventors: Steven Mahoney, Hillsboro, OR (US); Thomas Waters, Hillsboro, OR (US)

(73) Assignee: Serveron Corporation, Hillsboro, OR (US)

( * ) Notice: Subject to any disclaimer, the term of this patent is extended or adjusted under 35 U.S.C. 154(b) by 817 days.

(21) Appl. No.: 12/137,658

(22) Filed: Jun. 12, 2008

(65) Prior Publication Data

US 2009/0308246 A1 Dec. 17, 2009

(51) Int. Cl.
*B01D 53/22* (2006.01)
(52) U.S. Cl. .......................................... 96/6; 96/7; 95/46
(58) Field of Classification Search ............ 95/46; 96/6, 96/7
See application file for complete search history.

(56) References Cited

U.S. PATENT DOCUMENTS

| | | | |
|---|---|---|---|
| 3,523,408 A | 8/1970 | Rosenberg | |
| 4,070,167 A | 1/1978 | Barbee et al. | |
| 4,112,737 A | 9/1978 | Morgan | |
| 4,121,352 A | 10/1978 | Lameris | |
| 4,236,404 A | 12/1980 | Ketchum et al. | |
| 4,374,656 A | 2/1983 | Schrenker et al. | |
| 4,385,909 A | 5/1983 | Starr | |
| 4,402,211 A | 9/1983 | Sugawara et al. | |
| 4,404,102 A | 9/1983 | Pradel et al. | |
| 4,409,814 A | 10/1983 | Onuma et al. | |
| 4,437,082 A | 3/1984 | Walsh et al. | |
| 4,461,165 A | 7/1984 | Kesson | |
| 4,469,495 A | 9/1984 | Kiraizumi et al. | |
| 4,498,992 A | 2/1985 | Garrett, Jr. | |
| 4,561,866 A | 12/1985 | Altmann et al. | |
| 4,604,109 A | 8/1986 | Koslow | |
| 4,661,612 A | 4/1987 | George et al. | |
| 4,748,288 A | 5/1988 | Bitter et al. | |
| 4,763,514 A | 8/1988 | Naito et al. | |
| 4,764,344 A | 8/1988 | Knab | |
| 4,834,877 A | 5/1989 | Peters et al. | |
| 4,862,729 A | 9/1989 | Toda et al. | |
| 4,890,478 A | 1/1990 | Caiborne et al. | |
| 4,952,751 A | 8/1990 | Blume et al. | |
| 5,034,126 A | 7/1991 | Reddy et al. | |
| 5,104,810 A | 4/1992 | Birbara et al. | |
| 5,123,937 A * | 6/1992 | Shibata et al. | 95/46 |
| 5,154,832 A | 10/1992 | Yamamura et al. | |
| 5,222,118 A | 6/1993 | Gerth | |
| 5,243,848 A | 9/1993 | Cox et al. | |
| 5,290,340 A | 3/1994 | Gatten et al. | |
| 5,326,385 A * | 7/1994 | Rajani et al. | 95/46 |

(Continued)

OTHER PUBLICATIONS

International Search Report and Written Opinion from co-pending PCT application No. PCT/US2009/03413, Mailed Aug. 4, 2004.

*Primary Examiner* — Robert J Hill, Jr.
*Assistant Examiner* — Christopher P Jones
(74) *Attorney, Agent, or Firm* — Hancock Hughey LLP

(57) ABSTRACT

A gas extraction apparatus provides for reliable and accurate extraction of gases dissolved in fluids and routing the extracted gas to an analytical instrument. An extraction module comprises one or more fluorosilicone membranes molded into the shape of a flattened disk. The membranes are retained in a housing in a spaced apart relationship. The membrane is permeable to target gas(es), but not to the fluid. Porous support members support the membranes and prevent damage to them and the housing defines separate fluid flow paths for the fluid and the gas extracted from it.

12 Claims, 5 Drawing Sheets

U.S. PATENT DOCUMENTS

| | | |
|---|---|---|
| 5,340,384 A | 8/1994 | Sims |
| 5,372,634 A | 12/1994 | Monahan |
| 5,400,641 A | 3/1995 | Slemon et al. |
| 5,423,979 A | 6/1995 | Allen |
| 5,509,294 A | 4/1996 | Gowing |
| 5,509,954 A | 4/1996 | Derian et al. |
| 5,522,917 A | 6/1996 | Honda et al. |
| 5,584,416 A | 12/1996 | Florian |
| 5,659,126 A | 8/1997 | Farber |
| 5,663,492 A | 9/1997 | Alapati et al. |
| 5,686,657 A | 11/1997 | Craig et al. |
| 5,693,122 A | 12/1997 | Berndt |
| 5,749,942 A | 5/1998 | Mattis et al. |
| 5,749,945 A | 5/1998 | Beck |
| 5,753,126 A | 5/1998 | Rohwein |
| 5,762,684 A | 6/1998 | Hayashi et al. |
| 5,808,179 A | 9/1998 | Sittler et al. |
| 5,830,261 A | 11/1998 | Hamasaki et al. |
| 5,988,703 A | 11/1999 | Craig |
| 6,004,514 A | 12/1999 | Hikosa |
| 6,165,253 A | 12/2000 | Sirkar et al. |
| 6,258,154 B1 | 7/2001 | Berndt et al. |
| 6,365,105 B1 | 4/2002 | Waters et al. |
| 6,391,096 B1 | 5/2002 | Waters et al. |
| 6,432,051 B1 * | 8/2002 | Rantala ......................... 600/364 |
| 6,521,024 B1 * | 2/2003 | Akahori et al. ..................... 96/4 |
| 6,526,805 B1 | 3/2003 | Babes-Dornea et al. |
| 7,114,621 B2 | 10/2006 | Hester et al. |

\* cited by examiner

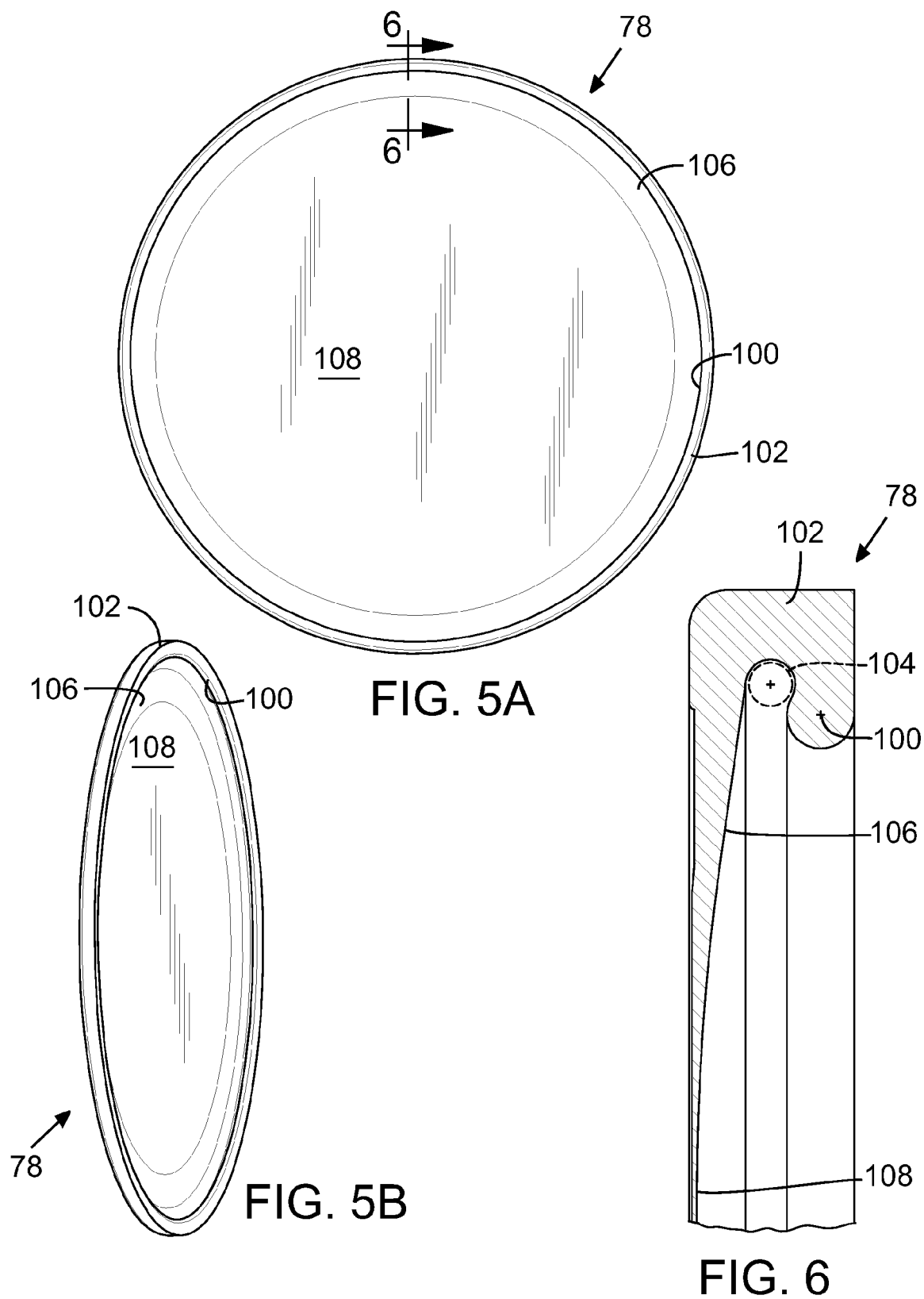

APPARATUS AND METHOD FOR EXTRACTING GAS FROM LIQUID

FIELD OF THE INVENTION

The present invention relates to apparatus and methods for extracting dissolved gases from liquid, and more particularly, the invention relates to an apparatus for extracting gases dissolved in electrical insulating oils.

BACKGROUND OF THE INVENTION

The electric power industry has for many years recognized that thermal decomposition of the oil and other insulating materials within oil-insulated electrical apparatus can lead to the generation of a number of "fault gases. These phenomena occur in equipment such as oil filled transformers (both conservator and gas-blanketed types), load tap changers, transformer windings, bushings and the like. The presence of fault gases may be a measure of the condition of the equipment. As such, detection of the presence of specific fault gases in electrical apparatus, and quantification of those gases can be an important part of a preventative maintenance program.

The presence of fault gases in oil-blanketed transformers with conservators and other utility assets has well documented implications relating to the performance and operating safety of the transformer. There is a substantial body of knowledge available correlating the presence of gases with certain, identified transformer conditions and faults. It is therefore beneficial to monitor the condition of dielectric fluids in electric equipment as a means to maximize performance, and at the same time minimize wear and tear on the equipment, and to thereby minimize maintenance costs and down time. Thus, information relating to the presence or absence of certain fault gases in transformer oil can lead to greatly increased efficiency in the operation of the transformer.

As an example, it is known that the presence of certain fault gases in transformer oil can be indicative of transformer malfunctions, such as arcing, partial or coronal discharge. These conditions can cause mineral transformer oils to decompose generating relatively large quantities of low molecular weight hydrocarbons such as methane, in addition to some higher molecular weight gases such as ethylene and acetylene. Such compounds are highly volatile, and in some instances they may accumulate in a transformer under relatively high pressure. This is a recipe for disaster. Left undetected or uncorrected, equipment faults can lead to an increased rate of degradation, and even to catastrophic explosion of the transformer. Transformer failure is a significantly expensive event for an electric utility, not only in terms of down time and the costs of replacement equipment, but also in terms of the costs associated with lost power transmission. On the other hand, by closely monitoring dissolved gases in transformer oil, the most efficient operating conditions for a given transformer can be actively monitored and the transformer load may be run at or near its optimum peak. Moreover, when dangerous operating conditions are detected the transformer can be taken off line for maintenance.

Despite the known need for reliable equipment to monitor gas in oil, designing equipment that holds up to the rigors of on-site conditions has been problematic for a variety of reasons. That said, there are a number of solutions known in the art. For example, mechanical/vacuum and membrane extraction methods and apparatus for degassing transformer oil are well known, as exemplified by U.S. Pat. No. 5,659,126. This patent discloses a method of sampling headspace gas in an electrical transformer, analyzing such gases according to a temperature and pressure dependent gas partition function, and based on the derived analysis predicting specific transformer faults.

An example of a gas extraction apparatus that relies upon a membrane tube for extraction of gas from transformer oil is disclosed in U.S. Pat. No. 4,112,737. This patent depicts a plurality of hollow membrane fibers, which are inserted directly into transformer oil in the transformer housing. The material used for the membrane is impermeable to oil, but gases dissolved in the oil permeate through the membrane into the hollow interior of the fibers. A portable analytical device such as a gas chromatograph is temporarily connected to the probe so that the test sample is swept from the extraction probe into the analytical device for analysis.

Although these devices have provided benefits, there are numerous practical problems remaining to the development of reliable apparatus for extraction, monitoring and analysis of fault gases in transformer oils. Many of these problems relate to the design of reliable fluid routing systems that are redundant enough to provide a relatively maintenance free unit. Since transformers are often located in exceedingly harsh environmental conditions, fluid routing problems are magnified. This is especially true given that the instruments needed to reliably analyze the gases are complex analytical instruments. Two patents that describe the difficulties of these engineering challenges are U.S. Pat. Nos. 6,391,096 and 6,365,105, which are owned by the assignee of this invention and both of which are incorporated herein by this reference. These two patents illustrate not only the complexities of the fluid routing systems needed, but solutions that have proved very reliable.

One of the most critical points in the analytical process is the extraction apparatus, where gas is actually separated from the electrical insulating oil. While there are several known apparatus for accomplishing this task, experience has shown that the extractor is one point where failure can occur. Stated another way, extraction devices to date have been more fragile than desired and cannot fully withstand the extreme conditions that are routinely encountered in field applications. As a result, additional support equipment or operation constraints are added to compensate for the performance shortcomings and to protect the extraction technology, which adds considerably to the cost. Despite advances in the technological solutions surrounding the extraction devices, especially those described in the '096 and '105 patents, there is a need for an extractor that is reliable and performs accurately under all conditions for substantial lengths of time without being monitored.

SUMMARY OF THE INVENTION

The advantages of the present invention are achieved in a first preferred and illustrated embodiment of a gas extraction apparatus that provides for reliable and accurate extraction of dissolved gases and for fluid-tight handling of both oil and extracted gas. The apparatus utilizes an extraction module comprising paired fluorosilicone membrane disks held in a housing. The membranes are permeable to target gas, but not to the insulating oil. The housing defines isolated oil and gas flow paths. The extraction module is connected to an analytical instrument such as a gas chromatograph for qualitative and quantitative analysis of the extracted gases.

In alternative embodiments, the extraction module may be built with multiple pairs of membrane disks, or a single membrane disk.

BRIEF DESCRIPTION OF THE DRAWINGS

The invention will be better understood and its numerous objects and advantages will be apparent by reference to the following detailed description of the invention when taken in conjunction with the following drawings.

FIG. 5A is plan view of a membrane separation disk of the type used in the gas extraction apparatus.

FIG. 5B is a perspective view of the membrane separation disk shown in FIG. 5A.

FIG. 6 is a cross sectional view of the membrane separation disk taken along the line 6-6 of FIG. 5A.

DETAILED DESCRIPTION OF PREFERRED AND ILLUSTRATED EMBODIMENTS

Figure 1:
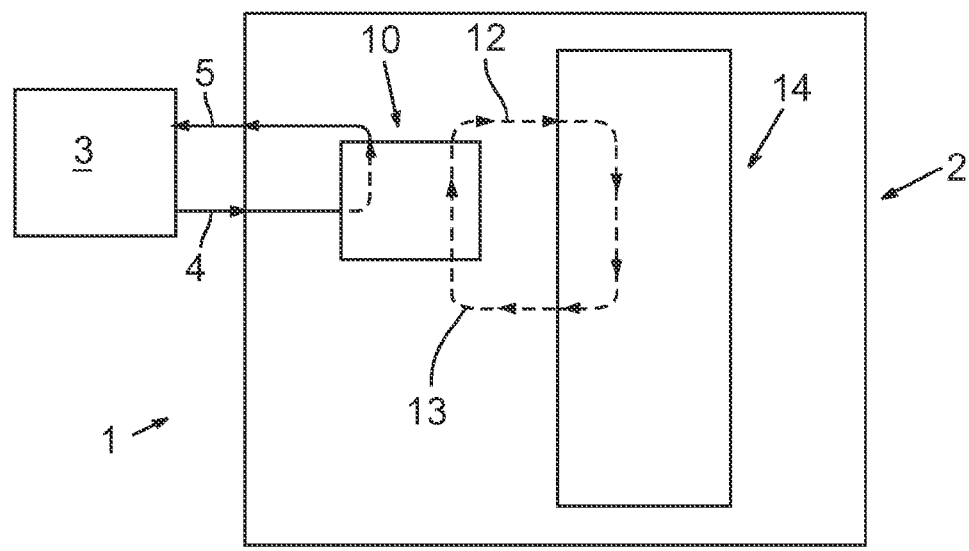
FIG. 1 is a simplified block diagram showing a system incorporating a gas extraction apparatus in accordance with the present invention.

The basic environment in which the gas extraction apparatus of the present invention is used and the significant components with which it is used will be described generally first to provide context, then a more detailed description of certain components will follow. With reference to FIG. 1 it may be seen that the gas extractor and analyzer 1 of the present invention is contained in a housing 2 that is located externally to the oil-filled or blanketed electrical device 3 that is being monitored. Electrical device 3 is typically a conservator or gas blanketed transformer, load tap changer, etc. A sample fluid supply line 4 is connected to electrical device 3 and delivers sample fluid to the components contained in housing 2. A sample fluid return line 5 likewise returns sample fluid to the electrical device from the analyzer 1. Extractor/analyzer 1 has been designed to be operable over extended periods of time without maintenance.

Following generally the flow of sample fluid within housing 2, fluid is routed into extractor assembly 10. Sample containing fluid (i.e. oil) flows through extractor assembly or module 10 in a manner detailed below, where gas dissolved in the oil is extracted into a second fluid phase for further processing. The oil from which gas has been extracted is returned to electrical device 3 through fluid return line 5. The gas that is extracted from the oil may be analyzed to determine the nature of the gases in the oil, or the extraction apparatus may be used to remove contaminants from the oil and thereby purify the oil.

Sample line 4 is preferably attached to electrical device 3 at a point of high oil flow to insure that a representative sample of fluid is always provided to extractor assembly 10. The location of the connection of the fluid return line 5 to electrical device 3 is not critical other than it being separated by a sufficient distance from the fluid supply line to not exchange substantially the same fluid. Specifically the fluid sample line can be attached to the oil fill valve on a transformer, a drain valve on an oil radiator, or an oil by-pass loop, for example. The fluid return line, on the other hand, may be attached to the bottom drain valve to return the oil to the transformer, or other suitable positions. Typically, there is no need to tap special ports into the transformer since the oil supply and return lines may be ported into existing locations.

As described below, the present invention relies upon principles of diffusion across a membrane to extract gases from a first fluid phase where the dissolved gases are in a relatively higher concentration, compared with a second fluid phase where the gases are in a relatively lower concentration. Typically, the first fluid phase is the transformer insulating oil and the second fluid phase is the gas volume contained within analysis components of the system.

Sample gas extracted from sample fluid flowing through the extractor assembly 10 is routed through tubing 12 to analytical instrument 14, which is an instrument configured for running automated qualitative and quantitative analysis of the gas samples delivered to it. Analytical instrument 14 may be one of several kinds of laboratory gas detection instrumentation, and is preferably a gas chromatograph that is designed for installation in a remote location and is automated by the control of a programmed computer. Analytical instrument 14 is thus referred to on occasion as gas chromatograph 14. Sample gas from analytical instrument 14 may be returned to extractor assembly 10 via tubing 13.

Figure 2:
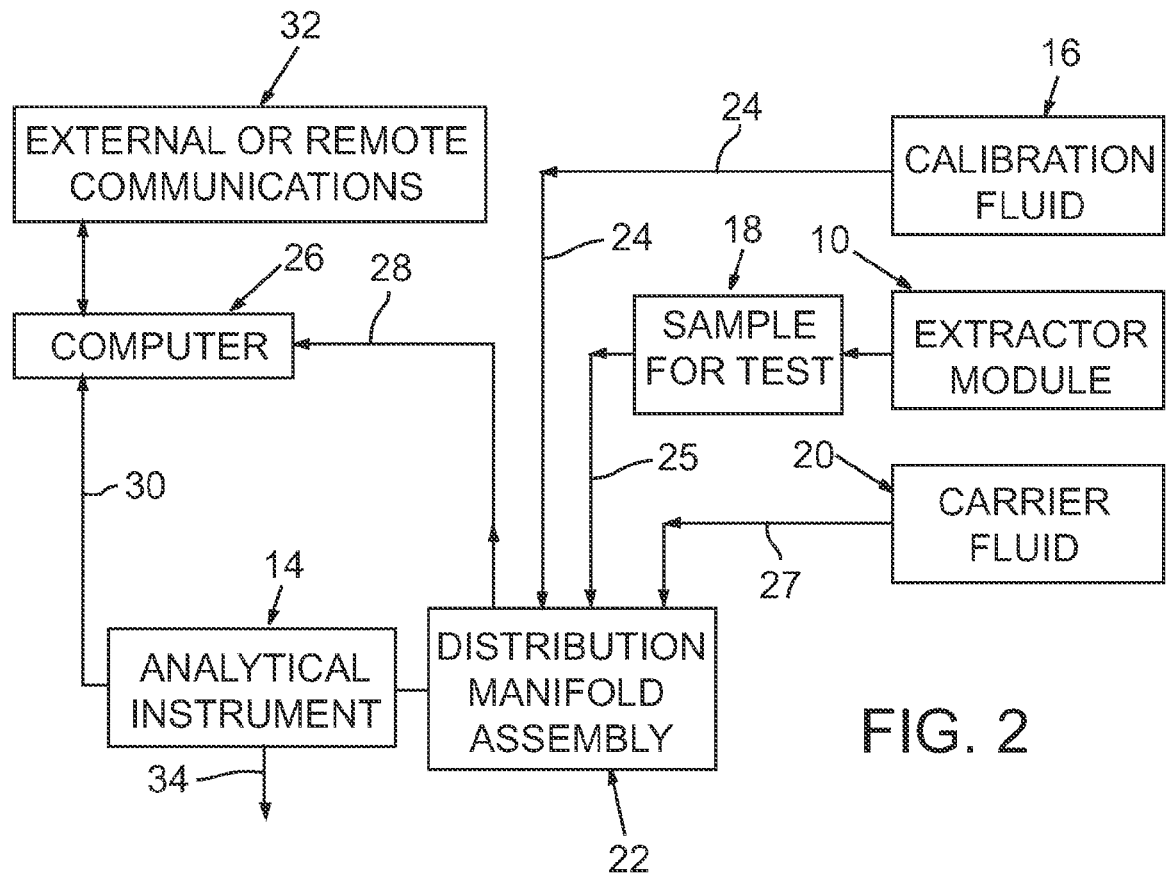
FIG. 2 is a simplified block diagram showing the gas extraction apparatus according to the present invention with significant other components with which the gas extraction apparatus is used.

With reference to FIG. 2, analytical instrument 14 is configured to work with computer systems 26 and external or remote communications equipment 32 so that analytical results may be acquired remotely. It should be noted that as used herein in the description of a preferred embodiment the word fluid refers to gases that flow through the instrument. However, the invention may be used with apparatus that use liquids and therefore the word fluid relates to any fluid that might be used in, and analyzed by, an analytical instrument.

As illustrated in FIG. 2, gas chromatograph 14 is fluidly connected to a source of calibration gas (fluid) 16, extractor module 10, which is the source of a sample for test 18 (i.e., the samples of gas extracted from oil in electrical device 3 that are to be analyzed), and a carrier fluid 20 which typically is supplied as a high pressure inert gas such as helium. Each of these sources of fluid (in this case the fluid is gaseous) is connected to a distribution manifold assembly, generally referenced with numeral 22. The fluid connections between the source fluids 16, 18 and 20 are accomplished with appropriate fluid lines 24 (which is the connection from calibration fluid 16 to distribution manifold assembly 22), 25 (the connection from sample for test 18 to distribution manifold assembly 22) and 27 (the connection from carrier fluid 20 to the distribution manifold assembly. These fluid lines are preferably stainless steel tubing. The fluid lines 24, 25 and 27 are fitted with appropriate passive fittings such as sealed compression ferrule-type fittings and the like. All connections between fluid lines 24, 25 and 27 and other components, such as components of distribution manifold 22, are fluid-tight connections with appropriate gaskets and O-rings and the like.

Distribution manifold assembly 22 does not form a part of the present invention and is not described in detail herein. However, a manifold assembly suitable for use with the present invention is described in detail in U.S. Pat. No. 6,391,096, which as noted above is incorporated herein by reference. Several components of the invention, including active fluid handling and control components are under the active control of a computer 26. Computer 26 is connected to and sends command signals to and receives data from components associated with distribution manifold assembly 22 by way of data lines 28. Computer 26 also controls operation of analytical instrument 14 through data lines 30. Computer 26 is connected to telephony or other remote or external communications systems equipment 32 so that computer 26 may be operated from a remote location, which thus allows the analytical instrument to be operated remotely and for data from the instrument to be acquired from a remote location. Computer 26 also controls the extractor control components which include circuitry and state machines that monitor and control the gas extraction module 10.

The word computer is used generically herein for a programmed device capable of controlling operations of extractor assembly 10 and gas chromatograph 14. Computer 26 will be appreciated therefore to encompass any microprocessor, microcontroller or other processor and associated hardware and software.

Sample aliquots of fluid that are to be analyzed are acquired and controlled by the fluid control and handling components of extractor/analyzer 1 and are injected into a gas chromatograph 14. The chromatograph 14 shown schematically in FIG. 1 is preferably a dual column chromatograph. The fluid control and handling components of distribution manifold assembly 22 fluidly route the sample aliquots to one of the selected separator columns.

Analyte separation in chromatograph 14 is carried on under controlled conditions as is well known in the art. For instance, the separation columns in the chromatograph are contained within a temperature-controlled cabinet. Likewise, all components of chromatograph 14 are contained within appropriate housings, none of which are shown in the figures but which will be understood as being necessary to perform reproducible and accurate analysis.

Gas chromatograph 14, as shown schematically in FIG. 2, includes a detector such as a thermal conductivity detector that is under the control of computer 26. Analytes separated in the chromatographic columns flow into and through the detector. Fluid flowing through the system such as carrier fluid and analyzed sample are exhausted to the atmosphere at exhaust port 34.

Analytical data compiled by gas chromatograph 14 from the analyzed sample is transmitted to computer 26 via data lines 30 where it is further processed according to software stored in the computer. Analytical results may then be transmitted from the computer 26 through remote communications equipment 32 on an automated basis, or the data may be acquired on prompt from a remote location.

Figure 3:
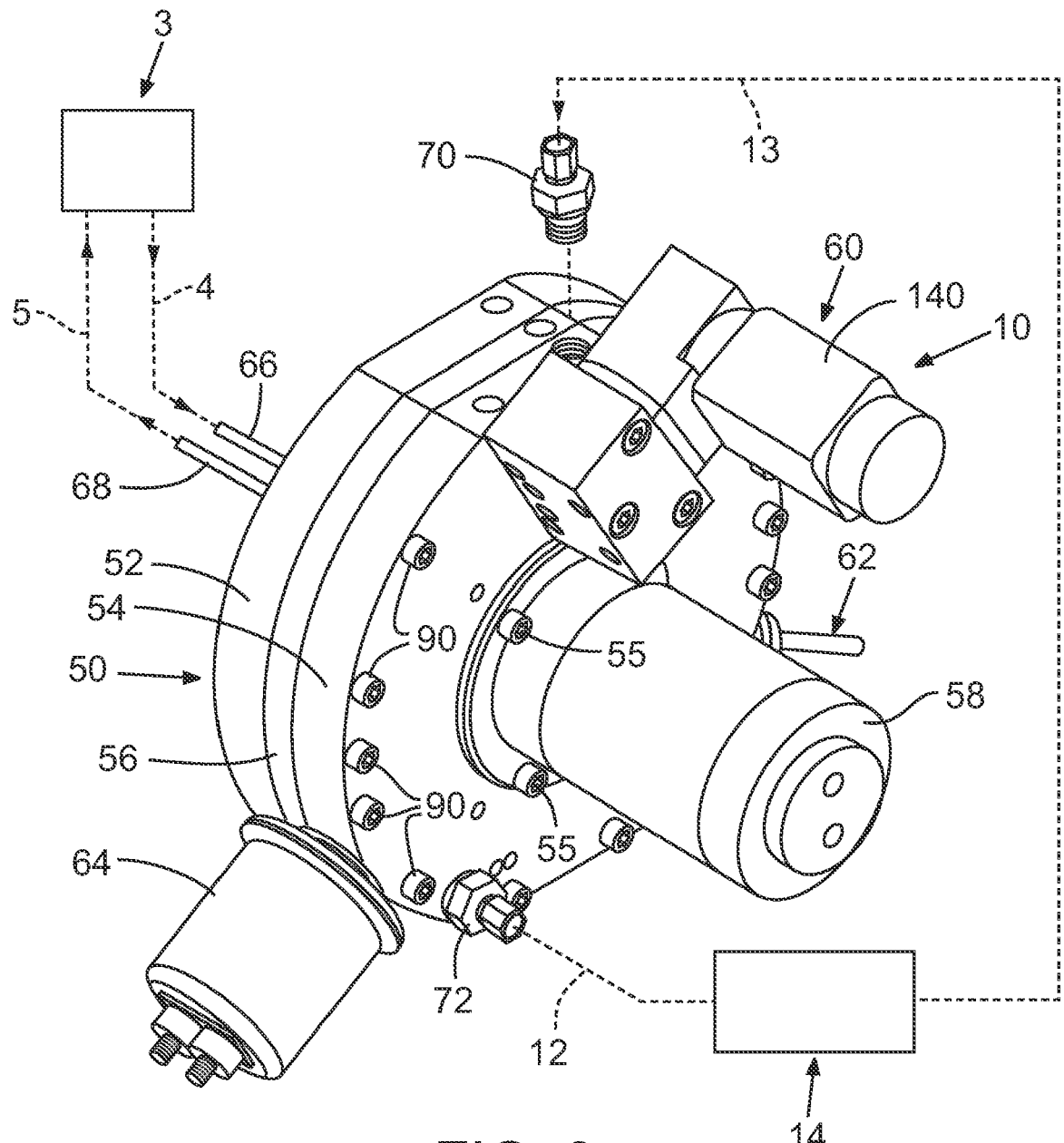
FIG. 3 is a perspective view of a preferred embodiment of the gas extraction apparatus according to the invention.

The construction of extractor assembly 10 will now be explained in detail with reference to FIGS. 3 and 4. At times, relative directional terms are used to describe the extractor assembly 10 and the positions of various components relative to other structures. Thus, the word "inner" or "inward" refers to the structural or geometric center of the extractor assembly 10. The word "outer" refers to the direction away from the geometric center. An "inner-facing" surface is a surface that faces the center of the assembly, and so on. Referring to FIG. 3, assembly 10 includes a generally cylindrical housing 50 that includes a first plate 52, a second plate 54, and a scarfing ring 56 sandwiched between the first and second plates. As detailed below, there are several component parts contained in housing 50, including the components that facilitate extraction of gas from the electrical insulating oil that is fed into extractor assembly 10, and various fluid flow paths for oil and extracted gas. An oil pump 58 is mounted centrally to second plate 54 with bolts 55 such that the pump controls the flow of oil through the extractor assembly 10. Also mounted to second plate 54 is a gas pump 60. An oil temperature sensor 62 is mounted to a side of second plate 54 and provides a means to monitor the temperature of oil or other fluid in the housing 50—the temperature sensor is threaded into a cooperative threaded opening in the housing. Temperature sensor 62 is preferably a standard thermocouple but could be any appropriate temperature sensing device. Finally, an oil pressure transducer 64 is mounted to a side of the second plate 54 so that the oil pressure in housing 50 may be monitored on an ongoing basis. The transducer also is threaded into a threaded opening in the housing. All of the foregoing components are attached to and under the control of the computer 26.

Shown schematically in FIG. 3 because the "lower" side of first plate 52 housing 50 is not visible in the perspective view of the drawing are an oil inlet 66 and an oil outlet 68 that are both connected to first plate 52. Oil inlet 66 is connected to oil sample fluid line 4 and oil outlet 68 is connected to oil sample return line 5. As detailed below, oil from electrical device 3 flows in a loop beginning with the electrical device, delivered through sample line 4 to extractor assembly 10 where gas in the oil is extracted, flows through housing 50, and is then returning to the electrical device via return line 5. Similarly, a gas inlet 70 and gas outlet 72 are attached to second plate 54. The oil and gas inlets and outlets just described are standard fittings that are threaded into the first and second plates, respectively. Gas inlet 70 is connected to tubing 13 and is thus the return line from analytical instrument 14. The gas outlet 72 is connected to tubing 12 and defines the sample delivery line to the analytical instrument. The gas extracted from oil flowing through extractor assembly 10 is pumped with gas pump 60 through outlet 72, through tubing 12 to analytical instrument 14, and depending upon the state operation, may be returned to extractor assembly 10 via tubing 13 and inlet 70.

All fittings and connections to housing 50 are leak free and utilize appropriate fittings and fluid-tight seal components such as O-rings and the like to ensure that there are no leaks.

Figure 4:
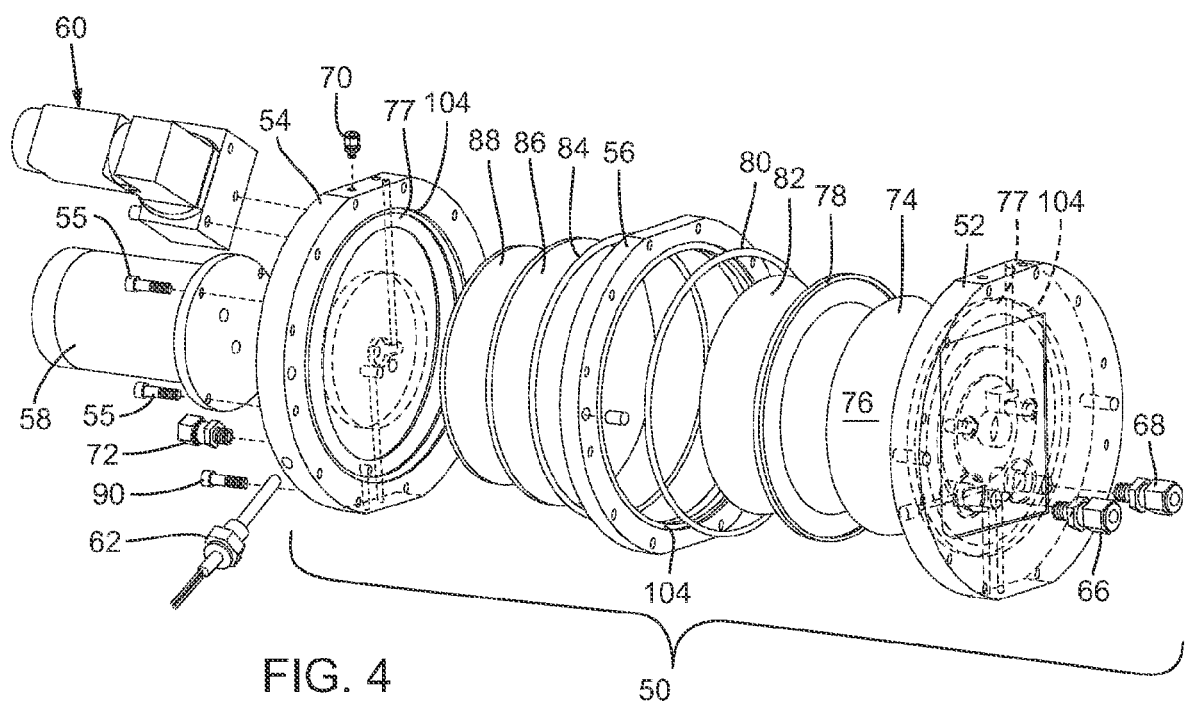
FIG. 4 is an exploded perspective view of the gas extraction apparatus shown in FIG. 3.

Turning now to FIG. 4, components of extractor assembly 10 will be described in detail. As noted previously, the primary components of housing 50 are first plate 52, second plate 54 and scarfing ring 56. Each of first and second plates 52 and 54 have fluid flow paths defined through them in the manner and for the purposes detailed below. Immediately adjacent first plate 52 is first frit 74. First frit 74 is a porous disk material through which oil and/or other liquids readily flow. Frit 74 is preferably sintered bronze but may be fabricated from other porous materials including sintered glass, sintered metals, or wire mesh and other materials. In the assembled extractor assembly 10 the first side 76 of first frit 74 is sealed around a perimeter thereof with adhesive to a cooperative seat 77 on the inner-facing side of first plate 52. Alternately, the seal between the first frit and the first plate may be facilitated with pressure applied between the two when the extractor assembly is bolted together. Adjacent first frit 74 is first membrane 78, which is attached and sealed around its perimeter in the manner described below to scarfing ring 56.

Identical components are stacked in a mirror image of those just described on the opposite side of scarfing ring 56. Thus, with continuing reference to FIG. 4, a second membrane 86 is attached and sealed around its perimeter to scarfing ring 56. A spacer layer 82 is positioned between first membrane 78 and second membrane 86. Spacer layer 82 provides a physical separation between the two membranes and is porous and inert to the analyte gases. The spacer layer 82 is preferably a porous paper material that is not degraded by the kinds of gases that are extracted from oil in the system described herein; filter-type papers have been found to work well but there are numerous other materials such as cotton and other fibrous pads that will work. The spacer layer 82 physically separates the two adjacent membranes 78 and 84 and thereby defines a space through which gas extracted from oil may flow, as detailed below.

A second frit 88, which is an identical material to that described above with respect to first frit 74 is attached to second plate 54, again in a manner identical to that described above with respect to first frit 74.

The components just described and shown in exploded format in FIG. 4 are sandwiched together in the assembled extractor 10 with a series of bolts 90 (one of which is shown in FIG. 4) around the perimeter of the plates 52 and 54. A first O-ring 80 between first plate 52 and scarfing ring 56, and a second O-ring 84 between second plate 54 and the opposite side of scarfing ring 56 insure that the extractor assembly 10 is leak-free when assembled. In addition, the O-rings reduce oxygen permutation from around the perimeter of the membranes 78 and 86 by isolating the membranes from the atmosphere.

The first and second membranes 78 and 86, respectively, will now be described with particular reference to FIGS. 5A, 5B and 6. Membranes 78 and 86 are preferably fabricated from a flexible material that is readily permeable to hydrocarbons having small molecular weight of the kind that are of interest to the present invention but which is impermeable to electrical insulating oils. The preferred material is a fluorosilicone material, which is very stable in a hydrocarbon environment such as electrical insulating oils. The membrane 78 is molded by pressing fluorosilicone material that has been blended with polymerizing agents into a mold. The polymerized membrane is removed from the mold and is cured by baking at elevated temperatures.

More specifically, a predetermined mass of fluorosilicone material is preformed into a flattened disk. This pancake-shaped disk is then inserted into a compression mold where it is heated, squeezed and pressed into a very thin disk shape having the thickness attributes desired. The mold is maintained at an elevated pressure and temperature until the fluorosilicone material cures, at which time the part is removed from the mold.

The membrane 78 defines a generally flattened circular disk that has a lip 100 defined around the outer peripheral edge 102. As best shown in FIG. 6, the outer peripheral edge 102 of membrane 78 is relatively thicker than the central portions of the membrane. The thickness of the membrane is greatest near the outer peripheral edge and gradually is reduced moving toward the center of the membrane. The membrane material is thus relatively thicker at a peripheral portion 106 where the typical thickness is about 0.020 inches. The thickness of the membrane gradually decreases moving inwardly across the central portion 108 of the membrane toward the center of the membrane, where the membrane material is thinnest, typically about 0.004 inches.

The lip 100 is configured to attach and seal to a cooperatively formed lip 104 on the inner-facing periphery of plates 52 and 54 (FIG. 4). Thus, on FIG. 6 the area of lip 104 of scarfing ring 56 to which lip 100 on the membrane 78 attaches is shown schematically with dashed lines. When membrane 78 is attached to plate 52, the membrane is stretched slightly so that the membrane material is slightly taught. This improves the fluid seal between the membrane and the plate to which it is attached, and removes any folds, wrinkles or creases in the membrane, which could cause a rupture or tear in the ultra-thin membrane web. Stretching the membrane in this manner thus improves the resistance of the membrane to development of leaks.

Figure 7:
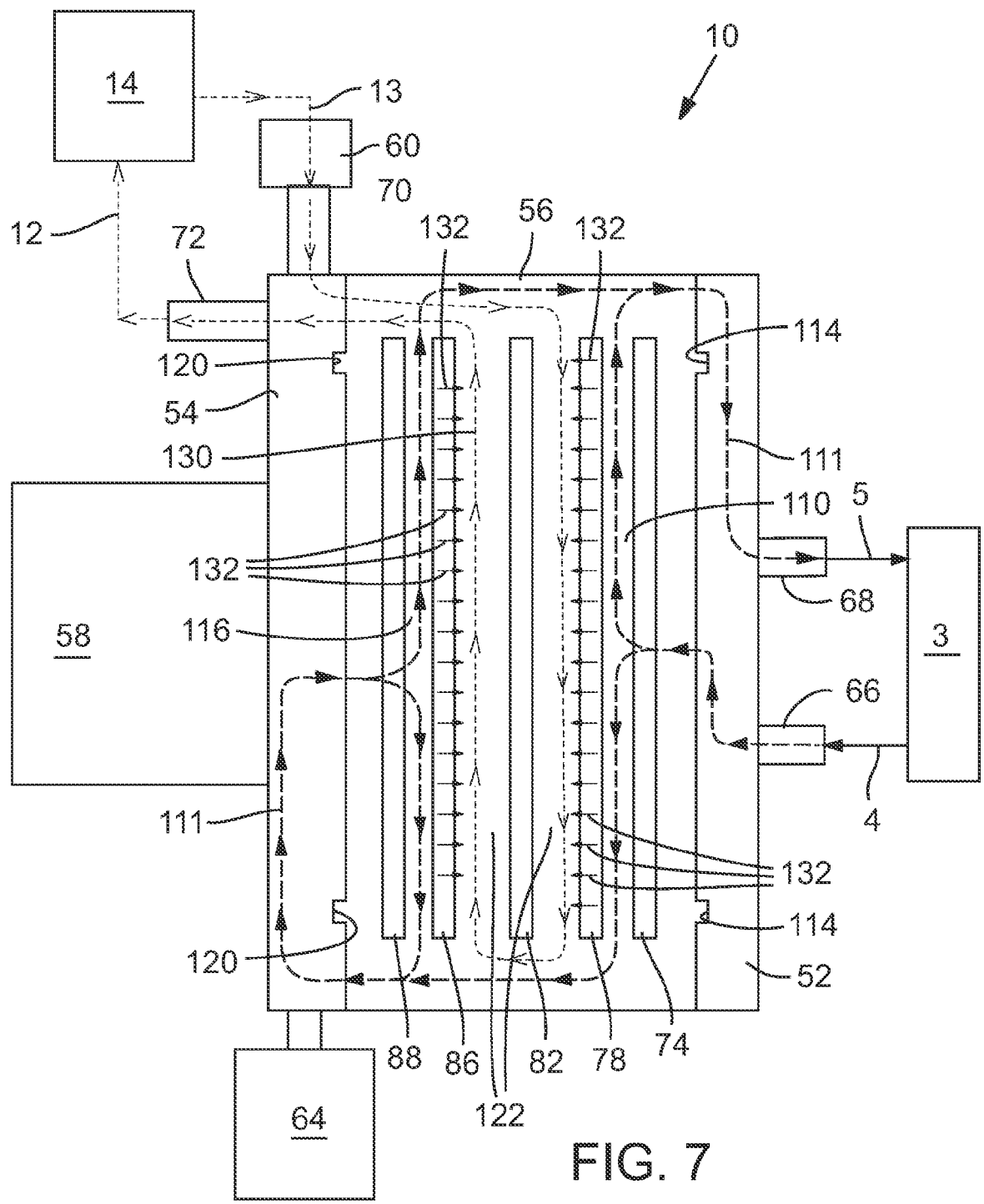
FIG. 7 is a schematic view of the flow paths for the first and second phases through the gas extraction apparatus.

Extractor assembly 10 is assembled with the components described above in the manner shown in FIG. 4 with bolts 90 so that the assembly is hermetically sealed and provides fluid-tight and leak free connections in all respects. Turning now to FIG. 7, which is highly schematic in order to show the various flow paths, plates 52, 54 and scarfing ring 56 define fluid flow paths through which oil and gas separated from the oil in the extractor assembly 10 flows. The flow paths through plates 52, 54 and scarfing ring 56 are defined by bores drilled through the plates. When the plates are assembled, the bores in the plates align and register with bores in the scarfing ring. O-rings are used to insure that the bores are leak free to define flow paths that are sealed.

Oil is delivered from electrical device 3 through sample line 4 and into extractor assembly 10 via oil inlet 66 and by virtue of operation of pump 58, which is fluidly connected to the oil bores through extractor assembly 10. In FIG. 7, the oil flow path through extractor assembly 10 is illustrated in dashed, relatively heavy, bold lines with solid arrowheads illustrating the general flow route. The oil flow path is assigned reference number 111. As noted previously, frit 74 is sealed to first plate 52 around the periphery of the frit disk, although this structural feature is not evident in the highly schematic view of FIG. 7. This defines a space 110 between the surface of the inner-facing side 76 of the frit 74 and outer-facing side of membrane 78 into which oil flows. The oil, which is under positive pressure by virtue of operation of pump 58, flows through the center of frit 74 and then across the facing surfaces of the frit and membrane 78. The oil tends to flow outwardly from the center of the membrane toward the outer periphery of the membrane and frit. A perimeter groove 114 located on the inner-facing surface of first plate 54 accumulates the oil. After the oil flows across the surface of membrane 78 and is returned to the transformer via bores that register with bores in scarfing ring 56 and first plate 52. The oil flow path 111 continues on the opposite side of scarfing ring 56 into second plate 54 and into a space 116 between the inner-facing surface of frit 88 and the outer-facing surface of second membrane 86. As with first frit 74, frit 88 is readily permeable to oil, and the oil flows through the frit and along the surface of the second membrane 86. Again, the oil tends to flow outwardly from the center of the membrane toward the outer periphery of the membrane and frit where groove 120 on the inner-facing surface of second plate 54 accumulates the oil. Oil flows through bores in plate 54 and scarfing ring 56 that that register with bores in first plate 52 to define a return flow path. The oil thus returns in a loop through first plate 52, through outlet 68 and to electrical device 3 by return line 5.

The oil flow through extractor assembly 10 defines a first phase. Gas extracted from the oil in the first phase forms a second phase; the flow path for the gas is illustrated in FIG. 7 with relatively lighter dashed lines with line-style arrow heads and is assigned reference number 130.

If a diffusion gradient is created across the two different phase sides, which are separated by first membrane 78 and second membrane 86, compounds of interest that exist in a higher concentration on one side of the membrane will diffuse across the membrane into the second phase side—the side with the lower concentration of that compound. That is, where oil in the first phase contains contaminants (such as fault gases) that are in relatively higher concentration on the first phase side than in the second phase, the contaminants diffuse across the phase barrier defined by the membranes to the second phase side (into the space 122 occupied by the porous paper spacer 82). Said another way, the contaminants in the first phase diffuse across the phase barrier defined by the membranes and into the second phase, where they reliably and reproducibly accumulate and are representative of and proportional to the concentration of the contaminants in the first phase. This is schematically illustrated by the "bold-line" arrows representing oil phase flow path 111 and the dashed arrows 130 representing the second phase side, or gas phase flow 130. As oil under pressure circulates through extraction apparatus 10, and more specifically, as the oil flows along the surfaces of the membranes, contaminants in the oil diffuse through the membranes and enter the gas phase 130. The contaminant (i.e., gas) diffusion across membranes 78 and 86 is illustrated with dashed arrows 132. The gas phase flow path 130 is isolated from oil phase flow path 111 and is defined by bores defined in plates 52 and 54, and scarfing ring 56. As noted earlier, spacer 82 between the adjacent membranes 78 and 86 maintains a space 122 into which the gas diffuses. Gas flow is initiated and maintained by a pump 60 (FIG. 4). As best shown in FIG. 7, sample gases from analytical apparatus 14 enter extractor assembly 10 through gas inlet 70 in second plate 54, and into gas phase flow path 130 through the spacer 82 (gas space 122), through gas pump 60 and is exhausted through gas outlet 72 and returned to analytical apparatus 14.

Operation of the system will now be detailed. As noted, oil flow is initiated by operation of pump 58, causing oil to flow in a circulating loop through oil phase flow path 111. As oil flows through the frits 74 and 88 and thus past and over the outer-facing surfaces or sides of membranes 78 and 86, gas diffuses through the membranes (reference number 132) into the space 122, which is defined by the spacer 82, and thus into gas phase flow path 130. The gas phase resulting from diffusion of gas molecules from the oil phase into the gas phase flows in a circulating loop through gas chromatograph 14; gas is circulated with the gas pump 60. Circulation of the oil phase and gas phase is allowed to continue until equilibrium in the concentration of gas exists on both sides of the phase barriers defined by membranes 78 and 86.

During the normal operation it is possible for the oil phase pressure to be less than the gas phase pressure. This may occur for several reasons, including aberrations in the operating conditions of the oil pump, external interference, etc. If a negative pressure does occur on the oil phase side, the membranes 78 and 86 tend to be "pulled" toward frits 74 and 88, respectively. The frits support the membranes and prevent membrane rupture if the membranes are pulled toward the frits.

Diffusion of compounds across the membranes is driven primarily by concentration gradients across the membranes. The time required to reach equilibrium or near equilibrium conditions depends upon factors such as gas concentration gradients and temperature, the volume of the gas being equilibrated, the thickness of the membrane, and the membrane surface area that is exposed to the oil. In addition, the flow rate of the oil carrying the gases affects the diffusion rate and thus the time required to reach equilibrium.

As noted earlier, contaminants of interest contained in oil filled device 3 are allowed to diffuse from the first liquid phase into the second fluid phase in extractor assembly 10. In this regard, during a sample equilibrium and acquisition phase oil is continuously circulated through the extractor assembly 10, returning as described earlier to the oil filled device 3. As the oil flows through the extractor assembly, dissolved gas contained in the oil diffuses across the membranes 78 and 86 into the second phase. This second phase, which comprises gaseous fluid, is circulated in either set time intervals or continuously to assure that all fluid in the second phase is homogeneous and until equilibrium conditions are reached. Stated otherwise, principles of diffusion dictate that the contaminants in the oil diffuse across the membrane from an area of relatively higher concentration to an area of relatively lower concentration until equilibrium (or conditions near to equilibrium) is reached.

As noted above, equilibrium and the rate of diffusion across the membranes are influenced by many different factors. In practice, it has been found that equilibrium using the extractor assembly 10 described herein is achieved in about 15 minutes with a total nominal gas volume of less than 7 cm$^3$l. This may be contrasted with the gas extraction apparatus described in the '105 and '096 patents, which required up to and greater than 1 hour with a nominal gas volume of up to 65 ml. It is apparent therefore that the present invention requires magnitudes less time to equilibrate, and magnitudes less volume of gas extracted from the oil phase than required by the patents just mentioned.

When computer 26 determines that it is appropriate to inject a sample of gas from the second phase into analytical instrument 14, or when computer 26 is prompted to do so externally, the continuous circulating loop of gas 130 is switched in distribution manifold 22 so that the sample gas is routed to the analytical instrument 14.

Typically simultaneously with the equilibration and sample acquisition step, and prior to operation of chromatograph 14, the system allows equilibration of the chromatograph 14 with pure carrier fluid 20, which as noted is typically an inert gas such as helium. This allows any fluid in the separation columns to elute and be flushed through the instrument and to be vented to atmosphere at 34. Sample gas is then injected into the chromatograph and gases present in the sample are qualitatively and quantitatively analyzed.

In the illustrated embodiment of the extractor 10 described above and shown in the attached drawings, the extractor uses two membranes housed in a housing defined by two plates and a scarfing ring. It will be appreciated that the fluid flow paths through the plates are configured so that additional pairs of plates, membranes and a scarfing ring may be stacked so that the capacity of the system and its speed increase. Thus, an extractor module may be defined as two membranes, two plates and a single scarfing ring. Multiple extractor modules may be stacked with the fluid pathways between modules communicating.

Similarly, an extractor module according to the present invention may be made using a single membrane. In this case, the extractor module is configured as shown in the figures with only a single membrane. The oil phase containing contaminants flows over the first side of a single membrane and the contaminants diffuse through the membrane 78 into a space defined by a spacer layer 82 that is positioned on the opposite side of membrane 78, thereby defining the physical separation between the single membrane 78 and the opposite wall of the module housing. As with the embodiment of FIG. 4, the spacer layer 82 physically separates the single membrane 78 from the adjacent wall of the module housing and thereby defines a second phase space through which gas extracted from oil may flow.

In view of the many possible embodiments to which the principles of our invention may be applied, it should be recognized that the detailed embodiments are illustrative only and should not be taken as limiting the scope of the invention. Rather, we claim as our invention all such embodiments as may come within the scope and spirit of the following claims and equivalents thereto.

The invention claimed is:

1. Apparatus for extracting gas from fluid, comprising:
   a housing defining a fluid pathway and a gas pathway that is isolated from the fluid pathway, said housing having an inlet into the fluid pathway and an outlet from the fluid pathway, and an inlet into the gas pathway and an outlet from the gas pathway;
   at least one separation membrane in the housing separating the fluid pathway from gas pathway, the at least one separation membrane comprising a fluorosilicone member that is substantially impermeable to the fluid and permeable to the gas, said separation membrane having a first side facing the fluid pathway and a second side facing the gas pathway and wherein the at least one separation membrane defines a generally flattened disk that is thicker at peripheral portion thereof and thinner at the center of the flattened disk;

a porous membrane support facing the first side of the separation membrane; and wherein the fluid pathway includes the first side of the at least one membrane.

2. The apparatus according to claim 1 wherein the at least one separation membrane is molded.

3. The apparatus according to claim 2 wherein the at least one separation membrane is retained in the housing under a stretched condition.

4. The apparatus according to claim 1 wherein fluid in said fluid pathway contains dissolved gas, and said gas diffuses from said fluid pathway through said membrane into said gas pathway.

5. The apparatus according to claim 1 having first and second separation membranes, each membrane having a first side and a second side, both of said membranes retained in the housing in a spaced apart relationship with the second side of the first membrane facing the second side of the second membrane to define a space between the at least two membranes and the space is in the gas pathway.

6. The apparatus according to claim 5 including a first porous membrane support on the first side of the first membrane and a second porous membrane support on the first side of the second membrane.

7. The apparatus according to claim 6 wherein the housing further comprises a first plate, a second plate, and a ring between said first and second plates, and wherein said first separation membrane is retained on the first plate and the second separation membrane is retained on the second plate.

8. The apparatus according to claim 7 wherein the first porous membrane support is adjacent said first plate and said second porous membrane support is adjacent said second plate.

9. The apparatus according to claim 8 wherein the first and second porous membrane supports are defined by sintered bronze frits.

10. The apparatus according to claim 9 further including a spacer between the second sides of the first and second membranes, said spacer in the gas pathway and permeable to gas, and said spacer maintaining the membranes in a spaced apart relationship.

11. The apparatus according to claim 10 wherein the spacer comprises paper.

12. The apparatus according to claim 5 including greater than two separation membranes.

* * * * *